United States Patent [19]

Kimmelman et al.

[11] Patent Number: 4,993,945

[45] Date of Patent: Feb. 19, 1991

[54] HEATED DENTAL MIRROR

[75] Inventors: Benedict B. Kimmelman, Melrose Park, Pa.; Erhart E. Demand, Boston, Mass.; Edmund Thelen, Strafford, Pa.

[73] Assignee: D-O Scientific Products, Inc., Philadelphia, Pa.

[21] Appl. No.: 388,258

[22] Filed: Aug. 1, 1989

[51] Int. Cl.⁵ ............................................. A61B 1/24
[52] U.S. Cl. ...................................... 433/30; 433/32; 219/219
[58] Field of Search .............. 433/30, 31, 32; 128/10, 128/11, 21, 22; 219/219; 350/640

[56] References Cited

U.S. PATENT DOCUMENTS

| | | | |
|---|---|---|---|
| 709,812 | 9/1902 | Bennett et al. | 219/219 |
| 1,036,000 | 8/1912 | Pease | 128/10 |
| 1,387,770 | 8/1921 | Dolbey | 433/31 X |
| 1,750,194 | 3/1930 | Rydman | |
| 1,764,455 | 6/1930 | Kulik | 433/31 |
| 1,934,110 | 11/1933 | Wilson | 32/27 |
| 2,120,091 | 6/1938 | Densten | 128/10 X |
| 2,428,975 | 10/1947 | Lamb | 240/6.4 |
| 2,525,181 | 10/1950 | Ransdell | 433/30 |
| 2,885,737 | 5/1959 | Wood, Jr. | 240/6.46 |
| 3,032,879 | 5/1962 | Lafitte | 433/30 |
| 3,300,859 | 1/1967 | Sanden | 32/69 |
| 4,090,506 | 5/1978 | Pilgrim | 433/31 |
| 4,212,105 | 6/1980 | Hukuba | 433/80 |
| 4,308,013 | 12/1981 | Major | 433/32 |
| 4,568,281 | 2/1986 | Harvey et al. | 433/30 |
| 4,872,838 | 10/1989 | Canter et al. | 433/31 |

FOREIGN PATENT DOCUMENTS

| | | | |
|---|---|---|---|
| 1932912 | 6/1969 | Fed. Rep. of Germany | 32/69 |
| 2341615 | 2/1975 | Fed. Rep. of Germany | 32/69 |

*Primary Examiner*—Robert P. Swiatek
*Assistant Examiner*—Nicholas D. Lucchesi
*Attorney, Agent, or Firm*—Eckert Seamans Cherin & Mellott

[57] ABSTRACT

A heated dental mirror is disclosed which includes in combination a handle portion and separable reflecting portion. The handle portion includes a hollow, cylindrical body within which are positioned a two cell electrically rechargeable battery. The body includes a first phone jack to facilitate recharging of the battery by employing a battery recharging stand. An electrical circuit is provided in the handle portion which includes an LED and a second phone jack wherein electrical energy from the battery will simultaneously energize both the LED and the second phone jack. The separable reflecting portion is removably connectable at the second phone jack to facilitate sterilization of the reflecting portion when desired. The reflecting portion includes a pair of first and second reflecting surfaces, one of which surfaces is positioned to receive and reflect illumination from the LED. An elongated mirror support shaft is wired to accommodate a resistance type electrical heater circuit, which circuit generates heat at all times when the reflecting portion is connected to the body portion. Heat energy from the heater circuit is thermally conducted to the first and second reflecting surfaces and sufficient heat is provided to elevate the temperature of the first and second reflecting surfaces to a temperature at or above the dew point temperature of the air in the patient's mouth.

17 Claims, 2 Drawing Sheets

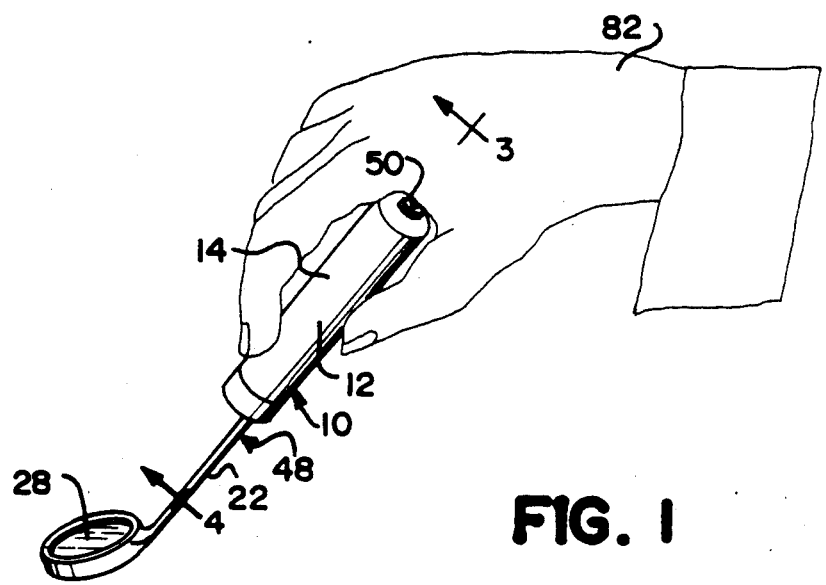
FIG. 1
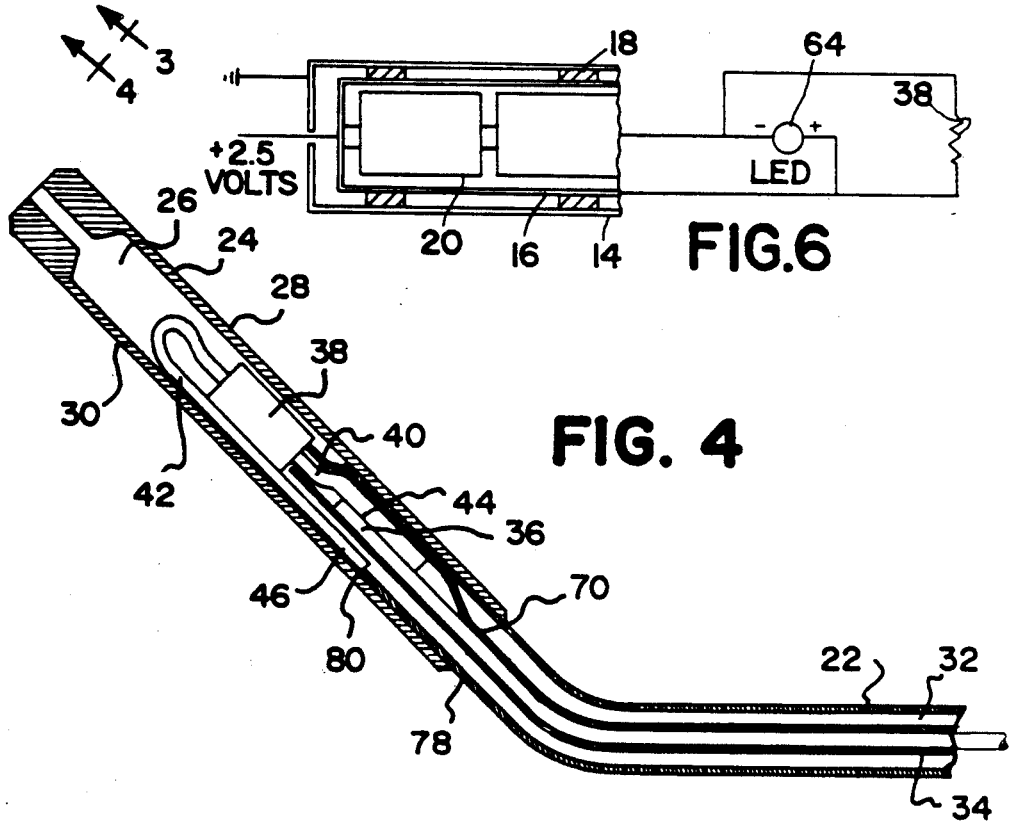
FIG. 6
FIG. 4
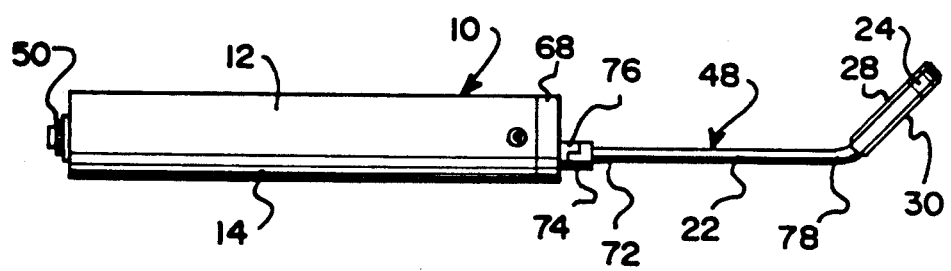
FIG. 2

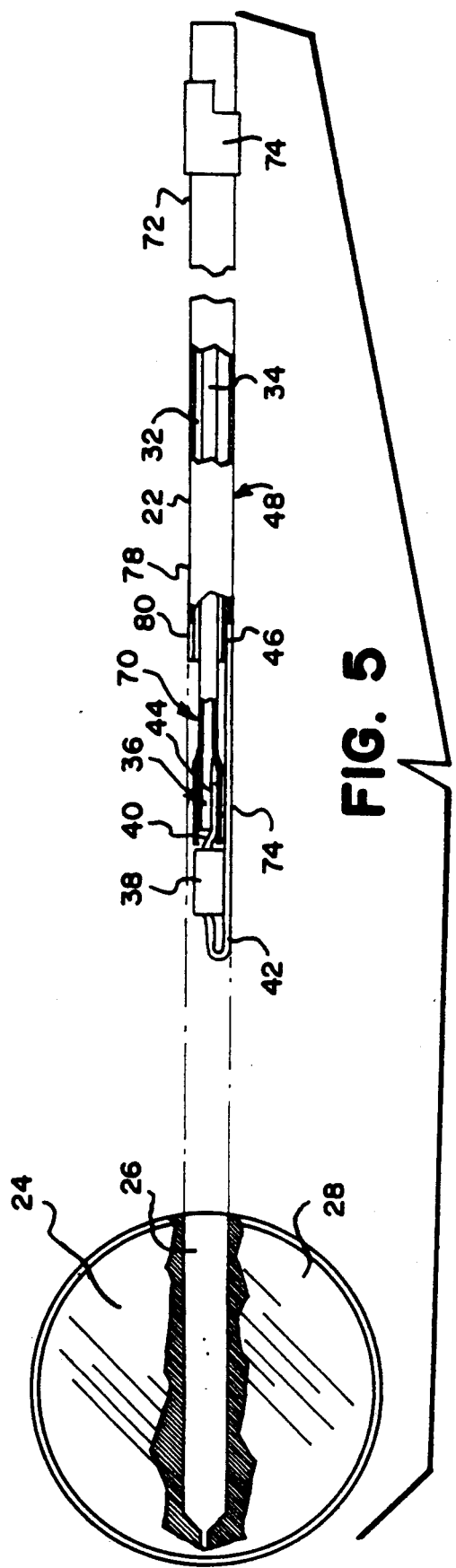
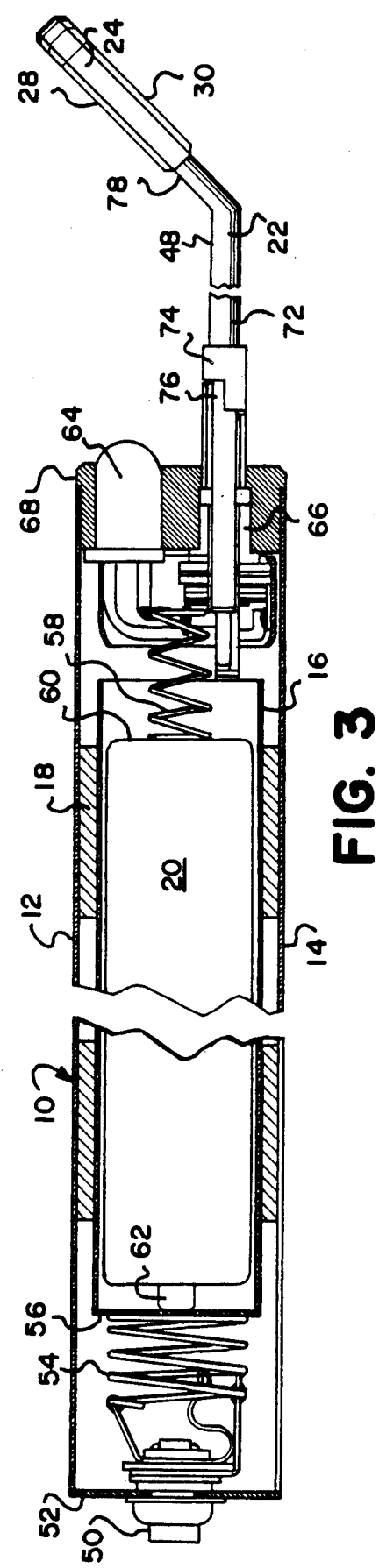

HEATED DENTAL MIRROR

BACKGROUND OF THE INVENTION

1. Field of the Invention

The present invention relates generally to the field of dental instruments, and more particularly, relates to an anti-fog type of dental mirror including a self-contained, portable, rechargeable energy source.

2. Discussion of the Prior Art

Mouth type mirrors or dental mirrors have long been in use by dentists and to a lesser extent, by physicians for conducting detailed examinations within a patient's mouth. Most frequently, the prior art type of dental mirrors have traditionally included an elongate handle having an angled, reflecting surface or mirror affixed at one end thereof. The entire instrument was sturdily constructed and was fabricated of materials suitable for sterilization whereby the device could repeatedly be employed for use with numerous patients with complete safety by simply adhering to recognized hygienic standards.

More recently, prior workers in the art have been developing dental mirrors having electrical components incorporated therein in efforts to improve operating capabilities. For example, in U.S. Pat. No. 1,750,194, Rydman disclosed a dental mirror comprising a tubular element or body having a battery accommodated therewithin. An electric light bulb was positioned forwardly of the body whereby light rays generated by the electric lamp could be directed by a reflector upon the forwardly positioned mirror.

In U.S. Pat. No. 2,428,975, Lamb discloses an illuminated dental mirror which includes generally a hollow, cylindrical body within which is housed a small dry cell battery and a flashlight type bulb. A transparent light transmitting member secures over the lamp, and at the remote end thereof, there is positioned a mirror for examination purposes. The light transmitting member is coated to prevent the escape of light in all but the desired direction.

Densten, U.S. Pat. No. 2,120,091 discloses a fogless dental mirror which includes generally a hollow handle which supports a forwardly positioned mirror. The stem of the handle is hollow and contains a heating element in the form of a resistance wire. A coupling receives heat from the conducting wire and is provided with a threaded connection to the mirror stem. The heat thus imparted to the instrument by the heating unit maintains the temperature of the mirror at substantially the same temperature as that of the mouth of the patient.

In U.S. Pat. No. 1,934,110, Wilson discloses a non-frosting type of dental mirror having a resistance type heater mounted within a metallic sleeve immediately beneath the reflecting mirror.

Harvey, et al, U.S. Pat. No. 4,568,281 discloses a heated dental mirror to prevent fogging including a mirror and a self-temperature regulated electronic heating element positioned immediately adjacent to the mirror. The device includes the necessary circuitry to precisely maintain the temperature of the mirror within a selected temperature range.

While the inventors of the above cited devices and others have generally addressed the problem of providing a non-fog type of oral examining dental mirror, such devices have proved to be relatively costly in construction, difficult to sterilize and in some instances, could possibly create safety problems due to direct connection to the usual 110 volt alternating current electrical power supply. Accordingly, the need remains to provide an improved, heated dental mirror that is simple in construction, completely safe in operation, readily rechargeable, and capable of easy sterilization, whereby the instrument can be constantly available for substantially continuous use with a plurality of patients.

SUMMARY OF THE INVENTION

The present invention relates generally to the field of dental instruments, and more particularly, is directed to an anti-fog dental mirror of the type incorporating one or more reflecting surfaces, a rechargeable battery, a resistance type heater mounted adjacent to the reflecting surfaces and illumination means to direct a light beam upon one of the reflecting surfaces at all times when the device is in use.

The heated dental mirror of the present invention comprises generally a hollow body within which is mounted a rechargeable battery to assure an extended period of trouble-free operation wherein the energy of the batteries can be repeatedly used to power both a resistance circuit of suitable electrical characteristics and capacity to safely heat a reflecting surface sufficiently to prevent fogging when placed within a patient's mouth and also to power a suitable light source to apply additional illumination upon the area of the patient's mouth that is being treated.

The battery is mounted within an elongate, hollow, cylindrical body, which body is equipped at one end thereof with a conventional jack of suitable design and construction to cooperate and electrically function with a conventional battery recharging stand. Mounted in the opposite end of the body is a low power source of subsequent illumination, such as an ultra bright light-emitting diode (LED), whereby light from the LED can be directed upon one of the reflecting surfaces for reflection and illumination of a portion of the patient's mouth, as controlled by the operator.

As employed herein, the terms "reflecting surface" and mirror are interchangeably used and are defined to mean any smooth surface whether constructed of glass, metal or other suitable material that is capable of reflecting an image for optimum mouth examination purposes.

A hollow, thin mirror support shaft extends forwardly of the body and terminates in a metallic or other heat transfer material mirror heater support. The mirror support shaft carries therewithin an electrical circuit wire as required to provide sufficient energy for heating directly at the site of the mirrors or reflectors. The electrical circuit includes a resistor of sufficiently small configuration to fit within the mirror heater support in an unobtrusive manner. Preferably, the reflecting surface or mirror of the present invention is dual in construction with one mirror surface provided on each face of the mirror heater support so that each side of the mirror heater support provides a suitable reflective surface. The mirrors of the present invention optionally may be either separate glass mirrors securely affixed to each face of the mirror heater support, or the opposed surfaces or sides of the mirror heater support can be highly polished in known manner to provide the required reflective surfaces.

A small heater or resistor is positioned interiorly of the mirror heater support and is designed to generate sufficient quantities of heat to elevate the temperature of the mirror heater support. The generated heat will be thermally conducted to the mirrored surfaces to essentially heat the reflecting surfaces to the same temperature as the human body, whereby there will be no tendency to fog or mist. This will then offer the dentist free and unobstructed observation of the area being treated at all times when the heated dental mirror of the present invention is in use.

It is a design feature of the present invention that the heat generated by the resistor will be just sufficient to elevate the temperature of the reflecting surfaces to the desired range (at or above the dew point temperature of the air inside the patient's mouth) without overheating, thereby positively preventing any possibility of unintentionally burning the patient. By properly sizing the resistor, it will convert a suitable quantity of electricity into heat so that the reflecting surfaces are maintained within the desired temperature range, without the danger of overheating.

Additionally, it should be noted that the heated dental mirror of the present invention employs only a low voltage, rechargeable, portable battery as the energy source. While the device is in use, there is therefore no possibility of the instrument ever carrying elevated voltages, for example, the usual 110 volt household current. In view of the construction features and the established high limit voltage of the battery of the present invention, there will accordingly be no possibility that a patient could ever be subjected to discomfort from an overly heated dental mirror or subject to electrical shock from an elevated voltage electrical energy source.

It is therefore an object of the present invention to provide an improved heated dental mirror of the type set forth.

It is another object of the present invention to provide a novel heated dental mirror which comprises a hollow body, one or more rechargeable cells retained within the body, a mirror support shaft extending from the body and carrying a low voltage electrical circuit including an electrical resistor, a mirror heater support secured to the mirror support shaft in manner to conduct heat from the electrical resistance circuit to the reflecting surfaces to prevent fogging when in use.

It is another object of the present invention to provide a novel heated dental mirror comprising a double sided reflecting surface, a light source directing rays of illumination upon one of the reflecting surfaces, a hollow mirror support shaft supporting the reflecting surfaces, the hollow support shaft enclosing an electrical circuit wire, a resistance element receiving low voltage current from the electrical circuit, the resistance element being positioned adjacent to the reflecting surfaces to apply heat generated by the resistor to the reflecting surfaces and a hollow body containing the rechargeable battery therein to power the light source and the resistance element whereby the reflecting surfaces and the source of illumination will be simultaneously and continuously operated when the heated dental mirror is in use.

It is another object of the present invention to provide a novel, removable, interchangeable, sterilizable mirror assembly.

It is another object of the present invention to provide a novel heated dental mirror that is simple in construction, inexpensive in manufacture and trouble-free when in use.

Other objects and a fuller understanding of the invention will be had by referring to the following description and claims of a preferred embodiment thereof, taken in conjunction with the accompanying drawings, wherein like referenced characters refer to similar parts throughout the several views and in which:

BRIEF DESCRIPTION OF THE DRAWINGS

FIG. 1 is a perspective view of the heated dental mirror of the present invention in use.

FIG. 2 is an enlarged, side elevational view of the heated dental mirror.

FIG. 3 is an enlarged, cross-sectional view taken along line 3—3 on FIG. 1, looking in the direction of the arrows.

FIG. 4 is an enlarged, cross sectional view of the mirror end of the invention taken along line 4—4 on FIG. 1, looking in the direction of the arrows.

FIG. 5 is an enlarged, partially, top plan view of the mirror section, and partially broken away to expose interior construction details.

FIG. 6 is a schematic electrical circuit in terms of the physical components of the heated dental mirror of the present invention.

DESCRIPTION OF THE PREFERRED EMBODIMENT OF THE INVENTION

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIGS. 1 and 2 a heated dental mirror 10 which comprises generally a handle or body portion 12 and a separable, sterilizable, cooperating reflecting or mirror portion 48. It is intended that the reflecting portion 48 be easily removable from association with the handle or body portion 12 whereby the removable portion can be readily sterilized or autoclaved to thereby render the device serially usable with a plurality of patients without fear of contamination.

Referring now to FIG. 3, the handle or body portion 12 comprises generally an outer casing 14 and an inner, battery containing casing 16, the inner and outer casings 14, 16 being electrically insulated from one another by suitable spacers, which may be in the form of insulating tapes 18. A conventional electrical current adapter, such as a telephone jack 50 is affixed outwardly of the outer casing bottom or head 52 to render the battery positioned within the inner casing 16 readily rechargeable by employing a conventional, low voltage, battery recharging stand (not shown) in the usual manner.

A suitable spring 54 biases between the jack 50 and the closed end 56 of the inner casing 16 and is properly electrically interconnected to conduct low voltage electrical charging current from the jack 50 to the inner casing 16 and thence to the battery 20. When the heated dental mirror 10 is not in use, it is intended that it will normally be stored within a conventional battery recharging stand (not shown) so that the battery 20 will be continuously recharged in well known manner.

A battery 20 comprising two cells, which preferably are of the rechargeable nickel-cadmium type, are retained within the hollow interior of the inner casing 16. A second spring 58 biases the remote end 60 of the battery 20 to urge the battery positive terminal 62 continuously into electrical contact with the electrically conductive closed inner casing end 56. In this manner, the battery 20 can be continuously charged at the recharging stand when the device is not in use. When in use, sufficient electrical stored energy will be provided by the battery 20 to function the electrical heater and electrical source of illumination of the heated dental mirror 10 for optimum use in the manner hereinafter more fully set forth. Optionally, if so desired, the rechargeable battery 20 and the battery recharging mechanism such as the recharging stand (not shown), the telephone jack 50 and the electrical connections to the spring 54 may be eliminated and replaced simply by a more conventional, replaceable battery, much in the manner of an ordinary flashlight. In such an alternate construction, after the anticipated effective use period of the battery has been approached, the spent battery could be discarded and simply replaced by a new battery.

Still referring to FIG. 3, low voltage electrical energy is fed from the battery 20 through the second spring 58 to an electrical circuit comprising in series or parallel arrangement a small illumination device, which may be an ultra bright LED 64 and a sub-miniature socket or phone jack 66. In this manner, when the battery 20 is charged, it is contemplated that both the LED 64 and the phone jack 66 will be continuously electrically energized so that the heated dental mirror 10 will be continuously available for use. Both the LED 64 and a portion of the phone jack 66 extend forwardly of the forward extension of the outer casing 12 and a protective end cap 68 may be affixed endwardly of the outer casing 12 in known manner.

Referring now to FIGS. 4 and 5, the reflecting or mirror portion 48 of the heated dental mirror 10 is illustrated. An elongate electrically conductive, mirror support shaft 22 is utilized which comprises generally a thin, sturdy, hollow, electrically conductive tubular body. The body defines a hollow interior 32 for receipt therein of an insulated bus wire 34 of suitable capacity for powering a low voltage heater circuit 70 for dental mirror heating purposes. In the illustrated embodiment, a twenty gauge insulated brass wire has been found to be electrically and mechanically suitable for this purpose. The mirror support shaft 22 terminates at its connected end 72 in a suitable connector 74 for releasable, current carrying interconnection with a cooperating connector 76 which forwardly extends from the body portion phone jack 66. The mirror support shaft 22 terminates at its mirror end 78 in a slot 80 to facilitate fabricating one connection of the heater circuit 70 as hereinafter more fully explained. The insulated brass wire in the shaft is glued to the inside of the shaft with a suitable sealant, such as RTV, which helps to seal the heater and the electrical circuitry from the sterilization liquids. The bus wire 34 is electrically insulated from the mirror support shaft 22 and is preferably completely enclosed and protected by the metallic portions of the mirror support shaft.

The heater circuit 70 comprises a suitable small resistor 38 of capacity to generate sufficient heat energy to elevate the temperature of the heated mirror support 26 and to heat the first and second reflecting surfaces 28, 30 to a temperature necessary to prevent fogging when the device is in use. Of course, normal body temperature is approximately 98.6 degrees F. and accordingly, the first and second reflecting surfaces 28, 30 should be heated to approximately this temperature or slightly higher prior to insertion of the reflecting portion 48 of the heated dental mirror 10 into a patient's mouth (not shown). A conventional resistor has been found suitable for this purpose. As shown, the usual leads 40, 42 of the resistor 38 securely affix respectively to one end 36 of the bus wire 34 and to a portion of the slot 80 of the mirror support shaft 22 by employing soldered or other connections 44, 46. Accordingly, when the connector 74 of the mirror support shaft 22 is properly seated within the cooperating connector 76 of the handle or body portion 12, electrical energy from the battery 20 will be applied to the resistor 38 by means of the bus wire 34, the metallic body of the mirror support shaft 22 and the heater circuit 70. As hereinbefore set forth, it is contemplated that the LED 64 will be simultaneously illuminated at all times.

As best seen in FIGS. 4 and 5, the portion of the heater circuit 70 which extends forwardly of the slot 80 in the mirror support shaft 22 is designed, sized and adapted to insert directly into the diametrically positioned cavity 26 which is formed in the heated mirror support 24 in a manner to provide a relatively tight engagement. Accordingly, heat generated upon electrical activation of the resistor 38 will conduct through the shaft attachment epoxy and the metallic material comprising the heated mirror support 24 directly to the first and second reflecting surfaces 28, 30. As indicated, the reflecting surfaces 28, 30 may be fabricated by polishing the front and rear faces of the heated mirror support 24 in known manner or, optionally, may be separate fitted glass mirrors which can be cemented or otherwise permanently affixed to the front and rear surfaces of the heated mirror support 24. In either type of construction, the heat generated by the resistor 38 will be applied directly upon the reflecting surfaces 28, 30 to thereby heat the reflecting surfaces to the desired temperature range to prevent fogging when the dental mirror 10 is in use. All portions of the cavity 36 not filled with the resistor 38 and other portions of the heater circuit 70 are filled with a suitable high thermal conductivity epoxy compound in known manner. Preferably, the resistor leads 40, 42 should be so sized shaped and positioned that the resistor 38 will be positioned substantially at the center of and equidistant from the pair of opposed, first and second reflecting surfaces 28, 30.

In use, the heated dental mirror 10 should normally be positioned and supported within a conventional battery recharging stand (not shown) which preferably may be wall mounted in the practitioner's office to thereby provide maximum accessibility while occupying the minimum amount of usable work space. At all times when the dental mirror 10 is positioned within the rechargeable stand, the battery 20 will be recharged in well known manner through electrical energy supplied to the phone jack 50 so that the instrument will always be ready for use. Upon taking the heated dental mirror 10 out of the rechargeable stand (not illustrated), the electrical energy stored within the battery 20 will remain continuously available to simultaneously illuminate the LED 64 and to energize the heater circuit 70 and the heating resistor 38.

The energization of the resistor 38 causes the heat of resistance to conduct through the metallic body of the heated mirror support 24 to reach the first and second reflective surfaces 28, 30. This conducted energy thereby heats these surfaces to approximately body temperature to thus eliminate any negative temperature differential between the reflecting surface and the dew point temperature of the air in the patient's mouth that may tend to cause fogging or misting on the reflecting surfaces 28, 30. As above set forth, no switch or other temperature control mechanism need be provided inasmuch as the size and capacity of the resistor 38 can be designed to provide sufficient quantities of heat to heat the reflecting surfaces 28, 30 to the necessary temperature and this temperature range will be maintained by the continuous dissipation of heat by radiation and conduction from the first and second reflecting surfaces 28, 30 and from other exposed areas of the heated mirror support 24.

When the heated mirror 10 is not being held by the hand 82 of dentist, it can then be returned to the battery recharging stand (not shown) with the phone jack 50 in direct contact with the usual contact element (not shown) of the recharging stand to function in the usual manner to keep the battery 20 charged. As hereinabove set forth, the reflecting or mirror portion 48 of the heated dental mirror 10 can be readily disassociated from or attached to the handle or body portion 12 by separating the mating connectors 74, 76 in the usual manner. Accordingly, the portion of the heated dental mirror that must be inserted into the patient's mouth can be readily removed and sterilized or otherwise treated without any damage whatsoever to the battery 20 or to the handle or body portion 12 whereby the device can be continuously used in conjunction with the treatment of a plurality of patients. In fact, even while the reflecting or mirror portion 48 is being sterilized, the battery can be recharged simply by positioning the handle or body portion 12 within the recharging stand (not illustrated).

Although the invention has been described with a certain degree of particularity, it is understood that the present disclosure has been made only by way of example and that numerous changes in the details of construction and the combination and arrangement of parts may be resorted to without departing from the spirit and scope of the invention. Thus, the scope of the invention should not be limited by the foregoing specification, but rather, only by the scope of the claims appended hereto.

What is claimed is:

1. A heated dental mirror comprising
   a body portion containing a low voltage battery therewithin;
   a first electrical circuit in the body portion and connected to receive low voltage electrical current from the battery,
      the first electrical circuit comprising a first connector and first and second electrical terminals;
   a reflecting portion removably connected to the body portion at the said first connector;
      the reflecting portion comprising an elongate mirror support shaft having two ends, a reflecting means affixed at one end of the mirror support shaft and a second connector affixed at the other end of the mirror support shaft, the second connector being adapted to be removably connected to the first connector, the reflecting portion comprising two electrical terminals corresponding to the first and second electrical terminals of the body portion, the two electrical terminals of the reflecting portion being adapted to respectively interconnect with the first and second terminals of the body portion when the first and second connectors are interconnected to lead the low voltage electrical current from the first electrical circuit to the reflecting portion;
   a second electrical circuit positioned in the reflecting portion, the second electrical circuit comprising a heater circuit constituting an electrical heating means,
      the second electrical circuit being protectively sealed and connected to the two electrical terminals of the reflecting portion to energize the electrical heating means when the first and second connectors are connected, the electrical heating means heating and elevating the temperature of the reflecting means when energized;
      the reflecting portion being sterilizable with the second electrical circuit protected from sterilization liquids;
   whereby a portable, low voltage, heated dental mirror can be continuously available for use.

2. The heated dental mirror of claim 1 wherein the mirror support shaft is hollow and wherein the second electrical circuit comprises a buss wire positioned within the hollow interior of the mirror support shaft.

3. The heated dental mirror of claim 2 wherein the buss wire connects to a portion of the electrical heating means and to one of the said electrical terminals of the reflecting portion.

4. The heated dental mirror of claim 3 wherein the mirror support shaft is fabricated of electrically conductive material and wherein each end of the mirror support shaft is connected respectively to the other of said electrical terminals of the reflecting portion and to the electrical heating means.

5. The heated dental mirror of claim 1 wherein the reflecting means comprises a cavity and wherein the electrical heating means is positioned within the cavity.

6. The heated dental mirror of claim 1 wherein the reflecting means comprises a mirror support having a pair of parallel faces and first and second reflecting surfaces provided at the said faces.

7. The heated dental mirror of claim 6 and a source of illumination mounted in the body portion, the source of illumination being electrically connected to the first electrical circuit, the source of illumination being continuously energized by the first electrical circuit.

8. The heated dental mirror of claim 7 wherein the source of illumination is positioned to direct its illumination upon one of the said reflecting surfaces.

9. The heated dental mirror of claim 7 wherein the source of the illumination is an LED.

10. A heated dental mirror comprising
    a generally hollow body portion, the body portion having a top, sidewalls depending from the top and defining an interior cavity, a bottom head defining the bottom of the body portion and a first connector;
    a battery positioned within the interior cavity, said battery producing a continuous supply of low voltage, direct electrical current;
    a first electrical circuit positioned within the body portion and drawing electrical current from the battery,
       said first electrical circuit comprising a first electrical terminal and a second electrical terminal;
    a reflecting portion removably connected to the body portion at the said first connector,
       the reflecting portion comprising a hollow mirror support shaft having two ends, one said end terminating in a second connector, the other support shaft end terminating in a reflecting surface connection;

a heater circuit secured to and protectively sealed within the mirror support shaft at the reflecting surface connection, the heater circuit comprising a heating means to generate heat and two electrical connections, one of said electrical connections extending through the hollow interior of the mirror support shaft and being electrically connectible to the first electrical terminal, the other said electrical connection being electrically connected to the mirror support shaft itself; and a mirror support connected to the mirror support shaft at the reflecting surface connection, the mirror support being positioned over a portion of the heater circuit, the mirror support receiving heat from the heating means and conducting the heat throughout the heated mirror support; and a first reflecting surface intimately provided on the mirror support, the first reflecting surface receiving a portion of the said heat from the heating means; and being heated thereby; and the reflecting portion being sterilizable with the second electrical circuit protected from sterilization liquids;

whereby heat from the heating circuit can be applied to the reflecting surface to elevate the temperature of the reflecting surface sufficiently to prevent fogging.

11. The heated dental mirror of claim 10 wherein the first electrical circuit comprises an LED, the LED being illuminated by electrical energy from the battery.

12. The heated dental mirror of claim 11 wherein the LED is positioned at the top of the body portion and wherein the light from the LED is directed upon the said first reflecting surface.

13. The heated dental mirror of claim 12 wherein the said heater circuit and the said LED are connected to always be energized simultaneously.

14. The heated dental mirror of claim 10 wherein the body portion comprises an electrical input jack, the jack being electrically connected to the battery to supply electrical current to the battery from an electrical source exterior of the heated dental mirror.

15. The heated dental mirror of claim 10 wherein the mirror support comprises a second reflecting surface, the second reflecting surface being spaced from and parallel to the said first reflecting surface.

16. The heated dental mirror of claim 15 wherein the heater circuit is positioned intermediate the first and second reflecting surfaces.

17. The heated dental mirror of claim 16 wherein the first and second reflecting surfaces are positioned equidistant to the heating means.

* * * * *